United States Patent
Popescu

(10) Patent No.: US 7,599,467 B2
(45) Date of Patent: Oct. 6, 2009

(54) DEVICE FOR CONTACT-FREE TRANSMISSION OF SIGNALS AND MEASURED DATA IN A COMPUTED TOMOGRAPHY APPARATUS

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/628,319

(22) PCT Filed: Jun. 3, 2004

(86) PCT No.: PCT/DE2004/001129

§ 371 (c)(1),
(2), (4) Date: Dec. 1, 2006

(87) PCT Pub. No.: WO2005/117706

PCT Pub. Date: Dec. 15, 2005

(65) Prior Publication Data

US 2007/0242798 A1    Oct. 18, 2007

(51) Int. Cl.
*A61B 6/00* (2006.01)
(52) U.S. Cl. .................... 378/21; 378/4; 378/5
(58) Field of Classification Search .................. 378/4, 378/15, 19, 205–207; 250/551, 217, 208.1; 329/350
See application file for complete search history.

(56) References Cited

U.S. PATENT DOCUMENTS

| 4,525,025 A | 6/1985 | Hohmann et al. |
| 4,996,435 A | 2/1991 | Keller |
| 5,287,117 A | 2/1994 | Posluszny |
| 5,577,026 A | 11/1996 | Gordon et al. |
| 6,178,024 B1 | 1/2001 | Degura |

FOREIGN PATENT DOCUMENTS

| DE | 195 43 386 | 3/1997 |
| DE | 198 60 909 A1 | 9/1999 |

OTHER PUBLICATIONS

VCSEL-Based Reflective Sensors Tackle More Demanding Applications, Tatum et al, LaserFocusWorld, Sep. 2003, pp. 79-83.

*Primary Examiner*—Irakli Kiknadze
(74) *Attorney, Agent, or Firm*—Schiff Hardin LLP

(57) ABSTRACT

An x-ray computed tomography apparatus has a stationary unit and a rotatable unit, carrying an x-ray source and a radiation detector. The rotatable unit rotates around an axis relative to the stationary unit, that proceeds through both units. In order to transmit signals and measured data between the rotating unit and the stationary unit, transmitting/reception devices are mounted at each unit. The transmitting/reception devices transmit directed signals and are automatically oriented toward each other during relative movement caused by rotation of the rotating unit with respect to the stationary unit.

19 Claims, 4 Drawing Sheets

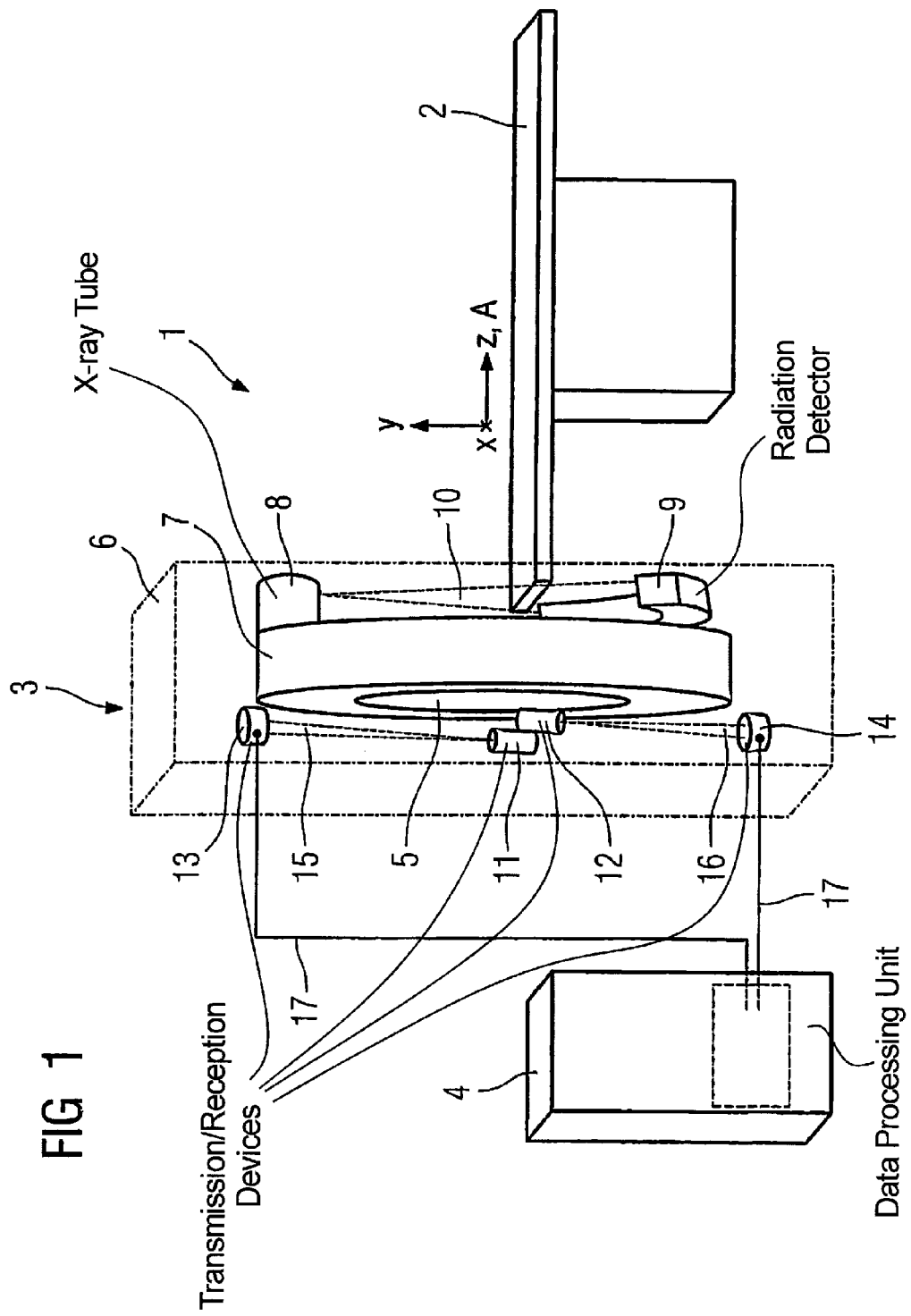

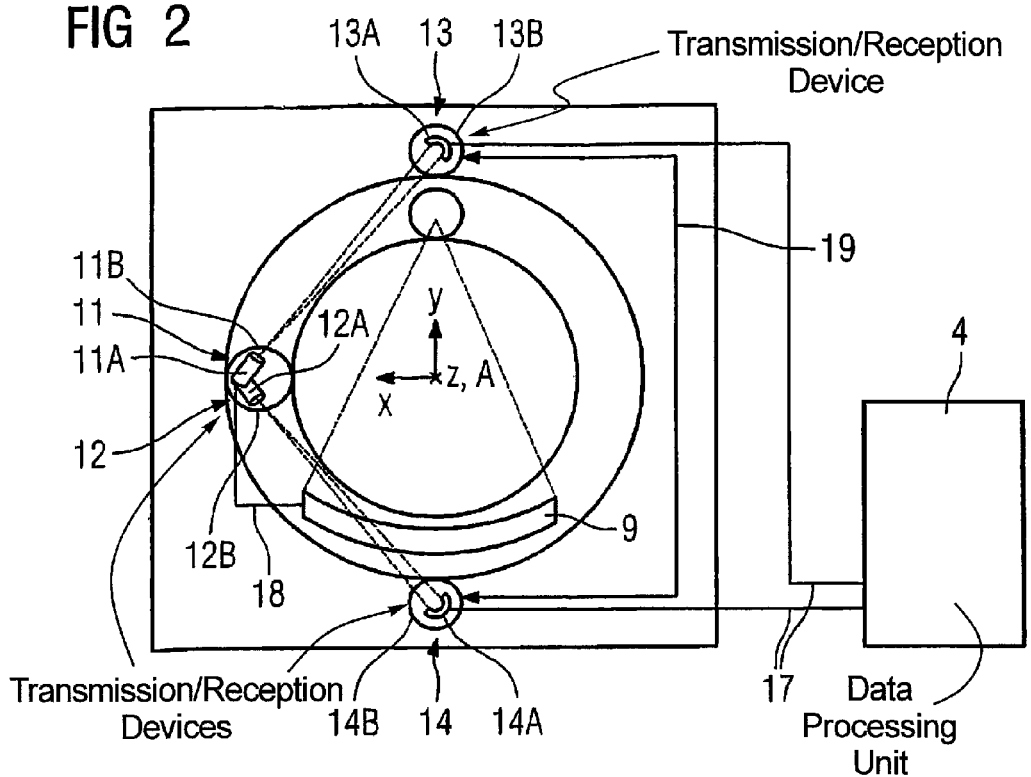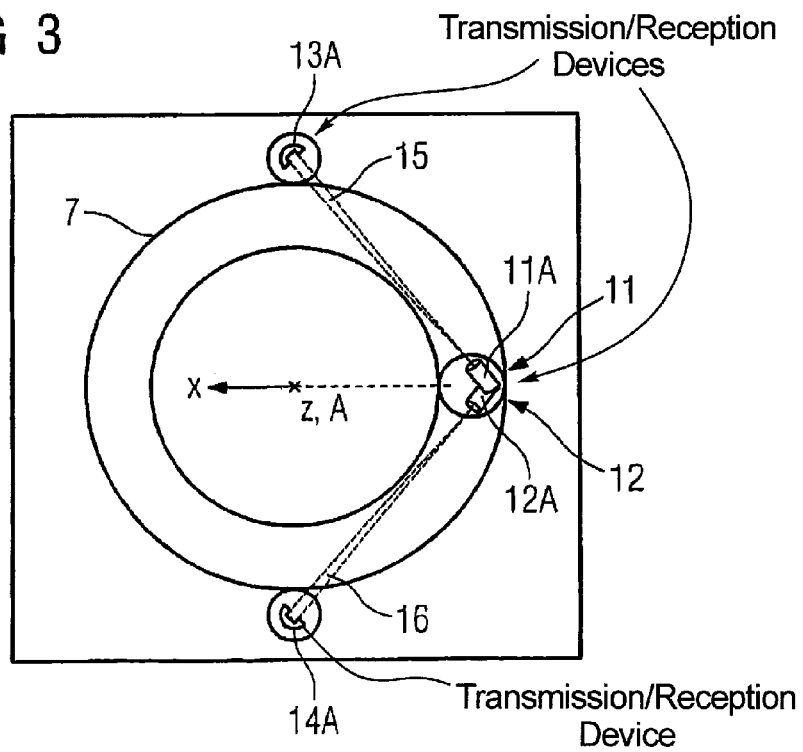

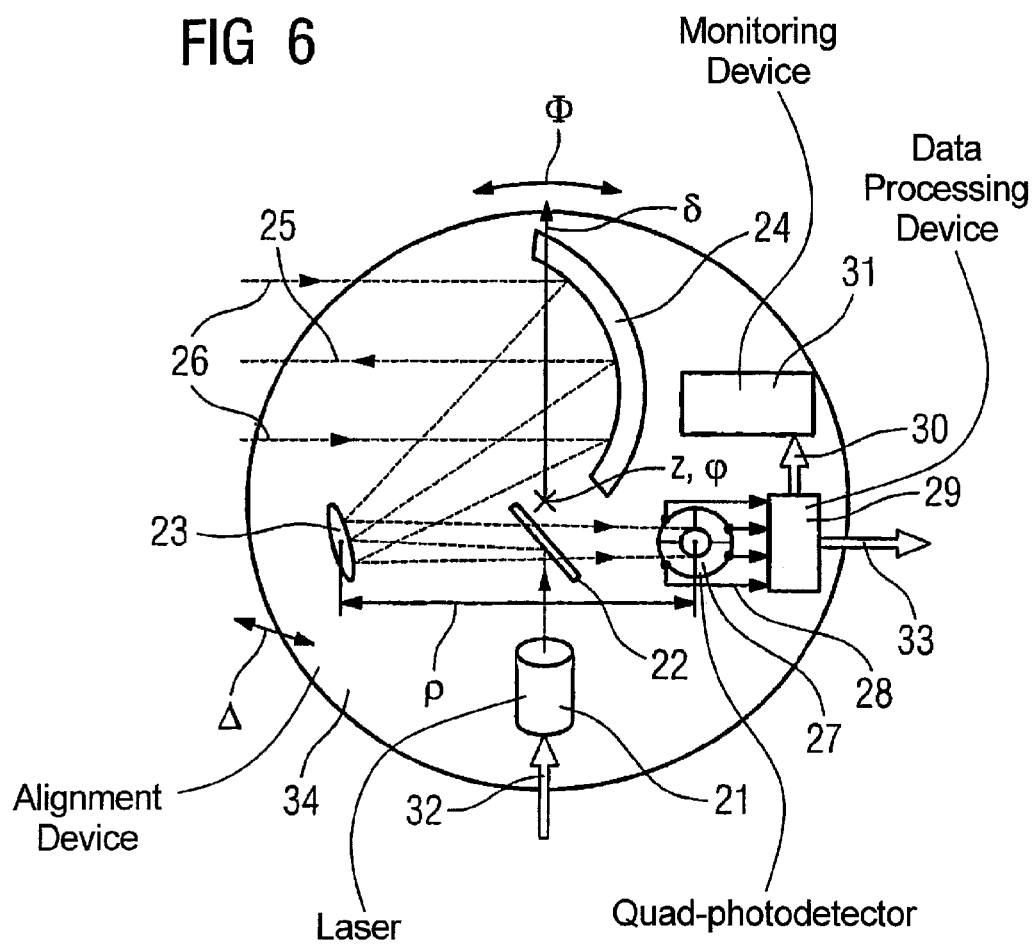

DEVICE FOR CONTACT-FREE TRANSMISSION OF SIGNALS AND MEASURED DATA IN A COMPUTED TOMOGRAPHY APPARATUS

BACKGROUND OF THE INVENTION

1. Field of the Invention

The invention concerns a device for contact-less transmission of signals and measurement data between a rotatable part and a stationary part in a computed tomography apparatus.

2. Description of the Prior Art

A device of the above type is known, for example, from U.S. Pat. No. 5,577,026. In this known device the signal is transmitted via antennas by means of electromagnetic radiation.

A shortening of the antennas is required to increase the data rate of the transmission. The shorter the antennas, the more susceptible the transmission of the signals to external influences such as, for example, interferences or electromagnetic interference fields. A shortening of the antennas causes quality losses in the transmitted signal.

For the transmission of signals via antennas as transmission/reception devices, a certain quantity of electromagnetic radiation is radiated into the environment. Electrical apparatuses and circuits located in the proximity of the transmission/reception devices can be disrupted. The transmission/reception devices must be adapted to electromagnetic compatibility standards.

Furthermore, a very good ground contact of the transmission/reception devices is always required in the known device. Otherwise the transmission can be significantly disrupted by common mode interference voltages.

A device in which the signals are transmitted between a rotor and a stator by means of optical light is known from U.S. Pat. No. 4,525,025. The signals are injected via light conductors into a ring located on the stator, this ring being provided with a reflecting inner surface for adaptation of the transmission/reception devices. The signals are detected by reception devices mounted on the rotor. In the case of very short pulses with high pulse power, non-linear effects (for example self phase modulations) and chromatic dispersive effects occur with increasing data rates. These effects are detrimental to the quality of the transmitted signals.

DE 195 43 386 describes a device in which the transmission of the signals ensues via an optical slip ring. The light must THEREBY cover paths of different lengths in the light conductor. With increasing data rates, non-linear and chromatic dispersive effects also occur that are detrimental to the quality of the transmitted signals.

Aside from this, in the known optical light devices surface roughnesses, mechanical production tolerances and mechanical vibrations of reflective surfaces cause a mode dispersion of the light and further impair the quality of the transmitted signals. Furthermore, the signal is attenuated by multiple reflections on reflecting surfaces.

SUMMARY OF THE INVENTION

An object of the invention to remedy the disadvantages according to the prior art by a device with which an improved transmission of signals and measurement data is possible. A further goal of the invention is to provide a device with which a high data rate can be transmitted.

The above object are achieved in accordance with the invention wherein a first transmission/reception device and a second transmission/reception device each have a transmission/reception unit for transmission and/or reception of a directed signal and a unit for automatic alignment of the transmission/reception unit thereof to the other transmission/reception unit, such that even given a movement of the second transmission/reception device relative to the first transmission/reception device the directed signal still can be transmitted. The transmission of the signal ensues directly between two transmission/reception devices. No signal conductor means (such as, for example, light conductors or multiple reflections on large mirror surfaces) are necessary for adaptation of transmission/reception devices. Absorption, non-linear and chromatic dispersive effects can be avoided. The quality of the transmitted signals can be distinctly improved.

Furthermore, the radiation of electromagnetic interference radiation is low given the transmission with directed rays. A disruption of electrical apparatuses located in the area can be significantly reduced. In particular the electromagnetic radiation exposure for a patient examined by computed tomography can be reduced.

In an embodiment of the invention, the stationary unit has two first transmission/reception devices and the x-ray detector has at least one second transmission/reception device. Alternatively, the stationary unit can have a first transmission/reception device and the rotating x-ray device can have two transmission/reception devices. In a CT x-ray examination a patient is typically located in the region of the central opening of the gantry of the scanner. As a result of this a signal transmission between a first transmission/reception device and a second transmission/reception device is not possible at every angle position of the rotatable x-ray device. With a suitable arrangement of, in total, three transmission/reception devices and a switching of the transmission/reception devices participating in the transmissions it is possible to transmit signals nearly continuously over the entire rotation angle of the gantry. The transmission can merely be briefly interrupted upon switching over. Such an interruption can be compensated, for example, by a buffering and a compression of the data to be transmitted.

In an embodiment of the invention, the stationary unit and the rotating x-ray device each have two transmission/reception devices. A suitable arrangement of, in total, four transmission/reception devices enables a continuous signal transmission between a first transmission/reception device and a second transmission/reception device over the entire rotation angle.

In a further embodiment of the invention, the transmission/reception devices of the stationary unit or of the x-ray device are azimuthally distributed approximately equally with regard to the z-axis. The angle range within which a signal transmission between a first transmission/reception device and a second transmission/reception device is possible thus can be enlarged. This is particularly possible for two transmission/reception devices mounted offset by an angle of approximately 180 degrees on the stationary unit. Two transmission/reception devices can analogously also be offset by an angle of approximately 180 degrees on the x-ray device.

In a further embodiment of the invention the transmission/reception devices of the stationary unit or of the x-ray device are mounted at an identical azimuthal angle with regard to the z-axis. Transmission/reception devices so arranged can be cabled in a simple manner and can be coupled with one another for data exchange. Fewer signal lines are required. Disruptions of the signals to be transmitted due to feed lines are reduced.

According to a further embodiment of the invention, the transmission/reception devices of the stationary unit and the transmission/reception devices of the rotatable x-ray device are respectively mounted with an equal radial separation from the z-axis. By a simple geometry of the arrangement of the transmission/reception devices it is possible to use alignment data of one transmission/reception device in a simple manner for alignment of another transmission/reception device.

According to a further embodiment, the transmission/reception devices of the stationary unit or of the rotating x-ray device are offset in the direction of the z-axis. A mutual influencing of transmission/reception devices thus can be avoided and an improved transmission can be achieved.

According to an embodiment, the transmission ensues between a transmission/reception device of the stationary unit with one transmission/reception device of the x-ray device. The transmission/reception devices can be combined into pairs, each including a first transmission/reception device and a second transmission/reception device. The effort in the alignment thus can be reduced and the alignment can be accelerated. In particular a mutual influencing of two pairs can be prevented in the transmission. For example, a specific frequency or modulation of the signals can be used for the transmission of the signals for each pair.

According to a further embodiment of the invention, the transmission of the directed signal ensues with optical light, preferably by means of laser light. The transmission can ensue, for example, with modulated laser light.

The optical light transmission of signals, in particular with laser light, enables a high data rate and quality of the transmitted signals.

Dry air barely absorbs light; dispersion therein is near 0. Moreover, no losses due to reflections and non-linear effects occurs as, for example, given light conductors and reflecting surfaces. The transmitted signals are barely attenuated.

In the case of laser light, the beam widening is particularly small. Laser light does not have to be refocused in a complicated manner such as, for example, in the case of transmission via light conductors and mirrored surfaces.

Furthermore, given the optical light transmission no electromagnetic interference fields are radiated. An adaptation of the transmission/reception devices to compatibility standards can be significantly simplified.

Alternatively, the transmission of the directed signal can ensue by means of electromagnetic waves, advantageously by means of radio or hertzian waves. The radiation of interference fields and the electromagnetic radiation exposure of the patient can be reduced.

If the transmission ensues with directional antennas (such as, for example, in radar), the directed electromagnetic waves can be radiated in the form of a conical beam. Reflections on the housing of the tomographic scanner as well as interferences can be avoided.

According to a further embodiment of the invention, the transmission/reception units are designed for bidirectional transmission of the signals. A transmission of acquisition data of the x-ray device to a data processing device and of control signals, operating data and measurement protocols to the x-ray device is therewith possible.

In a further embodiment of the invention, the transmission/reception units are fashioned such that the transmission ensues in the form of data packets of a fixed size. Data packets of a fixed size facilitate the handling and processing of sent and received signals. Transmission errors can be detected and corrected.

In another embodiment, an appending unit is provided for attachment of additional information to a data packet, advantageously in the form of header lines and/or footer lines. For example, a packet number can be added in the header line and a quality factor (such as, for example, a checksum, error detection code (cyclic redundancy check code) or error correction code (forward error correction code)) of a data packet can be added in the footer line. The additional information enables a simplified handling and processing of the data packets. The data packets can be identified using the packet numbers and be joined in a directed order. For example, in the case of data packets transmitted twice a decision can be made as to whether and which should be discarded. Transmission errors can be detected and corrected using the quality factor.

The header line or footer line can furthermore contain information about the type of the transmitted data, for example whether the data packet contains control signals or data produced by the detector.

According to a further embodiment of the invention, an encryption unit encrypts the data packets, advantageously according to 8B10B encryption. In 8B10B encryption an approximately constant signal intensity or light intensity is transmitted. The transmitted signals can thus be used for alignment of the transmission/reception devices. For example, without encryption a series of zero values of the intensity would be interpreted as a missing signal or incorrect alignment. Furthermore, the alignment units require no separate transmission/reception means. The transmission/reception devices can be built more simply and compact.

The 8B10B encryption of the data packets causes an increase of the number of the bits/s to be sent but the data rate of the transmission can be further reduced using compression methods.

According to a further embodiment of the invention, the transmission of the signals ensues with a data rate in the range of 1 to 100 gigabits per second (Gbps). Computed tomography systems with multi-line detectors, complicated acquisition protocols and control instructions require a reliable transmission with a high data rate. The inventive device enables a largely disruption-free transmission with data rates of 100 Gbps and more. The signals can be transmitted quickly and reliably even given short pulses and large data sets.

Furthermore, the alignment unit of the transmission/reception unit can include a detection unit for directed optical light signals or electromagnetic radio or hertzian waves. Optical light signals or electromagnetic waves can be used to monitor the alignment. It is in particular possible for the alignment unit to use the signals of the transmission/reception unit. No separate means for transmission of signals for alignment are necessary. In particular a mutual disruption of the signals of the alignment of the transmission/reception devices and the signals of the transmission of, for example, measurement data is avoided. The transmission/reception devices can be built simply, compact and cost-effectively.

Quadruple-photodetectors are particularly well suited for detection of direction changes of an optical light signal. These enable a precise and fast alignment and are particularly suitable for transmission/reception devices of a scanner rotating oppositely relative to one another.

DESCRIPTION OF THE DRAWINGS

FIG. 1 schematically illustrates the basic components of a computed tomography apparatus embodying a device for contact-free transmission of signals and measured data in accordance with the present invention.

FIG. 2 is a view through the computed tomography apparatus of FIG. 1 along the z-direction.

FIG. 3 illustrates a first embodiment for arrangement of the transmission-reception devices in accordance with the present invention.

FIG. 6 schematically illustrates components of a transmission/reception device in accordance with the present invention.

DESCRIPTION OF THE PREFERRED EMBODIMENTS

Figure 4:
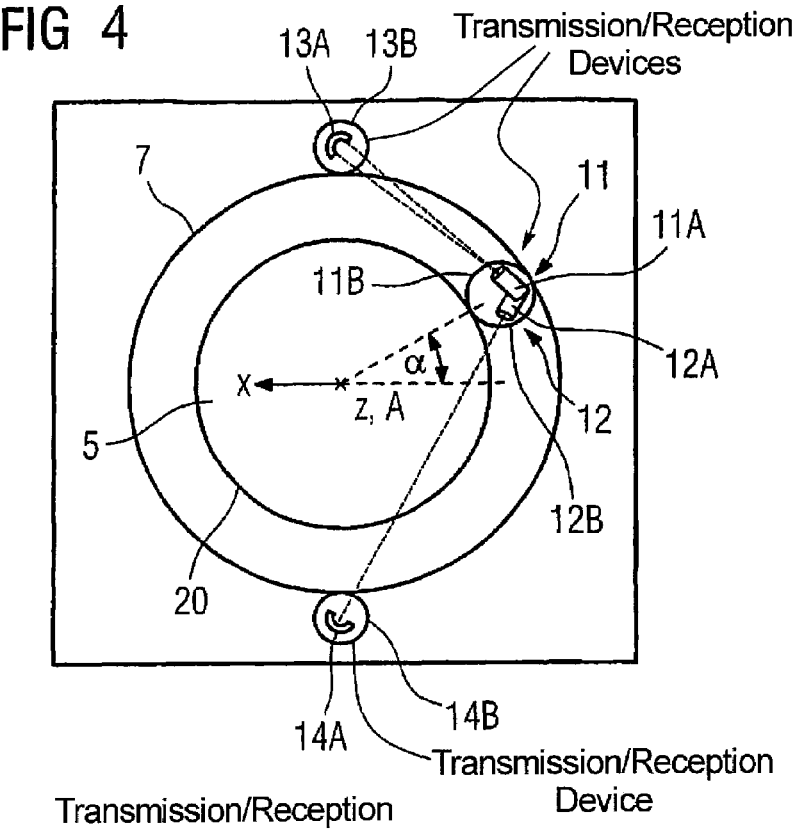
FIG. 4 illustrates a second embodiment for arrangement of the transmission/reception devices in accordance with the present invention.

For simplification, unidirectional transmission of signals is described. Transmission in the opposite direction ensues analogously. In particular a bidirectional transmission of signals is possible with the described device.

FIG. 1 shows a schematic design of a computed tomography scanner 1 with a patient bed 2, a gantry 3 and a data processing unit 4. The gantry 3 exhibits a central opening 5 into which the patient bed 2 with a patient located thereupon can be run in a z-direction given an examination. The gantry 3 has a stationary unit 6 and an x-ray device 7 rotatable around a z-axis A. The x-ray device 7 comprises an x-ray tube 8 and an oppositely-arranged detector 9. An x-ray beam emanating from the x-ray tube 8 is designated with the reference character 10. A second transmission/reception device 11 and a further second transmission/reception device 12 are mounted on the x-ray device 7. These are offset in the z-direction and mounted with the same radial separations and azimuthal angles with regard to the z-axis A. At the stationary unit 6 a first transmission/reception device 13 is mounted in an upper region. In a lower region a further transmission/reception device 14 is mounted offset by 180° from the z-axis A. the first transmission/reception device 13 and the further first transmission/reception device 14 are separated equally far from the z-axis A. A directed first laser beam 15 emanates from the second transmission/reception device 11 in the direction of the first transmission/reception device 13. A laser beam 16 directed in the direction of the further first transmission/reception device 14 emanates from the further transmission/reception device 12. The first transmission/reception device 13 and the further first transmission/reception device 14 of the stationary unit 16 are connected with the data processing unit 4 by means of first conductors 17. The reference characters x and y designate the x- and y-directions belonging to the z-direction z. The term "transmission/reception device" is abbreviated in the following with "SE".

The operation of the scanner is as follows:

In an x-ray tomographic examination the bed 2 with a patient thereon is moved in the z-direction such that the subject to be examined is located in the region of the central opening 5 of the gantry 3. Projection data of the examination subject are acquired for different angles with the x-ray device 7 rotatable around the z-axis A. The x-ray radiation 10 emanates from an x-ray tube 8 mounted on the x-ray device 7 and strikes the examination subject. The x-ray radiation not absorbed by the examination subject is detected by the detector 9 and transduced into digital electronic data. The data are transmitted from the x-ray device 7 to the stationary unit 6 by means of directed signals. The transmission of the signals between the second SE 11 and the first SE 13 ensues by means of the first directed laser beam 15. The transmission of the directed signals between the further second SE 12 and the further first SE 14 ensues by means of the second directed laser beam 16. The signals are transmitted in the form of encrypted data packets of a fixed size. For identification the data packets comprise a unique number in the header line, using which unique number the data packets are identified. A quality code is comprised in the footer line. The signals received from the first SE 13 and the further first SE 14 are respectively conducted to the data processing unit 4 by means of a first conductor 17 and are further processed by this data processing unit 4.

FIG. 2 shows a schematic view of the scanner 1 of FIG. 1 in the z-direction z. The second SE 11 and the further second SE 12 are connected with the detector via a second line 18. The first SE 13 and the further first SE 14 are connected with one another via a third line 19. The reference characters 11A, 12A, 13A and 14A designate a first, second, third and fourth transmission/reception means of the second SE 11, the further second SE 12, the first SE 13 and the further first SE 14. The reference characters 11B, 12B, 13B and 14B designate a first, second, third and fourth means for automatic alignment of the first, second, third and fourth transmission/reception means 11A, 12A, 13A and 14A. In the following the term "transmission/reception means" is abbreviated with "SEM". The term "the means for automatic alignment" is abbreviated with "AM".

In the shown arrangement of the further SE 11, the further SE 12, the first SE 13 and the further first SE 14, the first SEM 11A or, respectively, the third SEM 13A can directly transmit signals to the third SEM 13A or fourth SEM 14A. The first SEM 11A or the second SEM 12A transmit the data (received in the form of encrypted data packets of identical size) to the third SEM 13A or, respectively, the fourth SEM 14A. The data packets are decrypted by the data processing unit 4, combined in the correct order corresponding to their number and processed further. Data packets transmitted twice are additionally identified using the number. Those with the worse quality code are discarded.

Alignment data are exchanged via the third conductor 19 and via a connection (not shown) of the second SE 11 and the further second SE 12. These are taken into account together with the known symmetry of the arrangement of the second SE 11, the further second SE 12, the first SE 13 and the further first SE 14 given their alignment.

Figure 5:
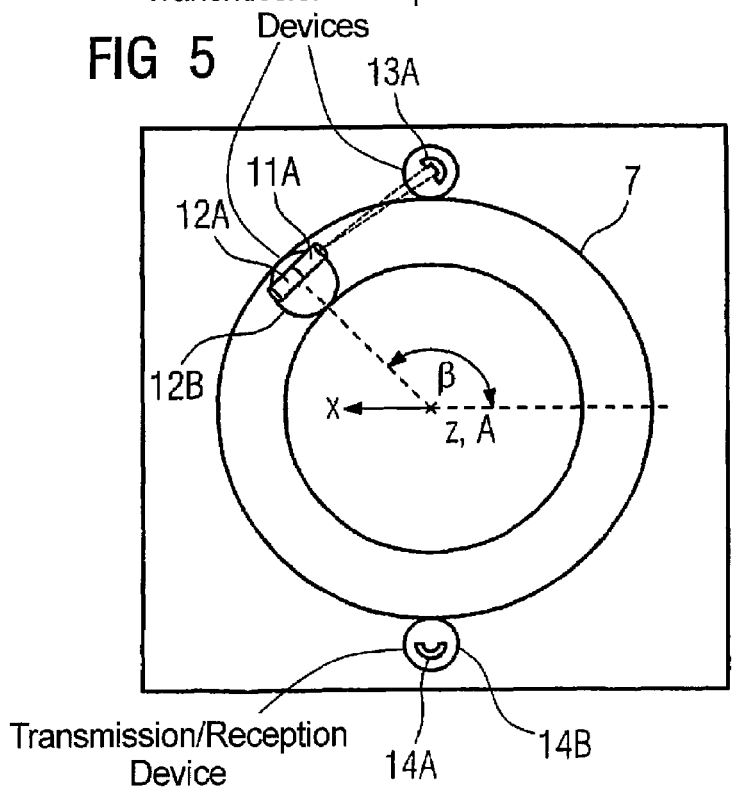
FIG. 5 illustrates a third embodiment for arrangement of the transmission/reception devices in accordance with the present invention.

A first, second and third arrangement of the second SE 11 and further second SE 12. mounted on the x-ray device 7 are shown in FIG. 3 through FIG. 5. In FIG. 3, with regard to the z-axis A the second SE 11 and further second SE 12 located are at an angle of 0° relative to the negative x-direction x. These are rotated counter-clockwise around the z-axis A by an angle α of 30° in FIG. 4 and by an angle β of 135° in FIG. 5.

In FIG. 3 the first SEM 11A transmits data packets to the third SEM 13A by means of the directed signals 15 and 16. The second SEM 12A transmits no data packets to the fourth SEM 14A.

In FIG. 4 the x-ray device 7 is shown rotated counterclockwise by an angle α=30° relative to the position in FIG. 3. Given the rotation the first through fourth AM 11B through 14B automatically align the first through fourth SEM 11A through 14A to one another. During the rotation from the position in FIG. 3 to the position in FIG. 4, the first SEM 11A can always transmit signals to the third SEM 13A. Given the rotation from the first position to the second position, the signal transmission between the second SEM 12A and the fourth SEM 14A is increasingly disrupted by the housing 20 rotating around the central opening 5. The transmission of the data packets is increasingly faulty. As of a first angle a signal transfer between the second SEM 12A and the fourth SEM 14A is no longer possible. The second SEM 12A and the fourth SEM 14A are deactivated. The data packets are exclusively transmitted via the first SEM 11A and the third SEM 13A.

In FIG. 5 the x-ray device 7 is shown rotated counterclockwise by an angle β=135° relative to the position in FIG. 4. Exclusively the first SEM 11A transmits data packets to the third SEM 13A. The second SEM 12A and the fourth SEM 14A are inactive. If the x-ray device rotates further, a signal transmission between the second SEM 12A and the fourth SEM 14A is possible at a second angle. These are activated upon reaching the second angle and the alignment is initiated. Stored alignment data of the first through fourth SEM 11A through 14A are thereby used. Given further rotation, the second SEM 12A and the fourth SEM 14A are automatically aligned to one another by the second AM12B and the fourth AM14b, respectively. The signal transmission between the second SEM 12A and the fourth SEM 14A is improved upon further rotation. If the x-ray device 7 rotates counterclockwise beyond the position shown in FIG. 2, at a third angle the signal transmission between the first SEM 11A and the third SEM 13A is disrupted. The quality of the transmission between the first SEM 11A and the third SEM 13A drops. After deactivation of the first and third SEMs 11A and 13A, the transmission of the data packets ensues exclusively via the second SEM 12A and the fourth SEM 14A.

FIG. 6 schematically shows a design of a transmission/reception device. A dichromatic mirror 22, a movable convex mirror 23 and a concave mirror 24 are arranged in succession in the beam path of a laser 21. A modulated laser beam emanating from the laser is designated with the reference character 25. An incoming modulated laser beam is designated with the reference character 26. Located in its beam path at a distance ρ from the convex mirror 23 is a quad-photodetector 27. The quad-photodetector 27 is connected with a data processing device 29 with four conductors 28. This is connected with a monitoring device 31 with a fifth conductor 30. An incoming data line and an outgoing data line are designated with the reference characters 32 and 33. The data lines are connected with the laser 21 or the data processing device 29. The transmission/reception device is arranged on an alignment device 34. The reference character Φ designates a first rotation of the alignment device 34 around a φ-axis φ. The reference character Δ designates a second rotation of the alignment device 34 around a δ-axis δ.

The operation of the transmission/reception device is as follows:

The laser 21 of the transmission/reception means receives an incoming signal via the incoming data line 32. Corresponding to the signal the laser emits the outgoing, modulated laser beam 25. The laser beam 25 is radiated from the transmission/reception means via the dichromatic mirror 22, the convex mirror 23 and the concave mirror 24 and transmitted to a further transmission/reception means.

The transmission/reception means simultaneously receives the incoming modulated laser beam 26. The laser beam 26 is focused onto a quad-photodetector 27 via the concave mirror and 24 the convex mirror 23 without being deflected by the dichromatic mirror 22. The quad-photodetector 27 possesses four active quadrants for detection of the incoming laser beam 26. Each quadrant is connected with the data processing device 29 via a fourth line 28. The laser beam 26 detected by the quadrants is transduced into a signal by the data processing device 29 and forwarded via the outgoing data line 33.

Am oppositely-ensuing rotation of two communicating, active transmission/reception means changes their position relative to one another. A change of the distance between the transmission/reception means alters the size of the focus on the quad-photodetector 27. A variation of the signals of the quadrants is connected with this.

Furthermore, the focus on the quad-photodetector 27 is shifted due to the rotation of the focus. A change of the signals of the quadrants is thereby likewise caused.

The data processing device 29 receives the signals of the quadrants and generates three error signals. The error signals are relayed via the fifth conductor 30 to the monitoring device 31. Via control loops and electronic actuators (not shown) arranged on the alignment device 34, the alignment of the transmission/reception means is altered such that the error signals are minimized and a best possible transmission of signals is ensured. A minimization of the error signals is achieved in that the actuators adapt the focus length ρ for compensation of an altered separation of two transmission/reception means, implement a first rotation φ around the φ-axis φ for compensation of an altered azimuthal angle with regard to the z-axis and implement a second rotation Δ around the δ-axis δ for compensation of misalignments in the z-direction z.

Previously stored alignment data of the transmission/reception means as well as alignment data of other transmission/reception means can be drawn upon for alignment. The alignment is thereby accelerated and the transmission of the signals is improved.

Although modifications and changes may be suggested by those skilled in the art, it is the invention of the inventors to embody within the patent warranted heron all changes and modifications as reasonably and properly come within the scope of their contribution to the art.

I claim as my invention:

1. An x-ray computed tomography apparatus comprising:
   a stationary unit;
   a rotatable unit mounted for rotation relative to said stationary unit around a rotational axis that proceeds through both said stationary unit and said rotatable unit;
   an x-ray source and a radiation detector mounted on said rotatable unit; and
   a device for contact-free transmission of signals and measured data between said rotatable unit and said stationary unit comprising two first transmission/reception devices mounted on the stationary unit and two second transmission/reception devices mounted on the rotatable unit, each of said first and second transmission/reception devices comprising a transmission/reception unit that transmits or receives a directed signal and an alignment unit that automatically aligns at least one of the two first transmission/reception devices to at least one of said two first transmission/reception devices, causing said directed signal to be transmitted between the aligned ones of said first and second transmission/reception devices during rotation of said rotational unit relative to said stationary unit.

2. An x-ray computed tomography apparatus as claimed in claim 1 wherein said at least one first transmission/reception device and said at least one second transmission/reception device are approximately equally azimuthally distributed around said rotational axis.

3. An x-ray computed tomography apparatus as claimed in claim 2 comprising two first transmission/reception devices at said stationary unit mounted at 180° from each other.

4. An x-ray computed tomography apparatus as claimed in claim 1 comprising two second transmission/reception devices at said rotatable unit disposed 180t° from each other.

5. An x-ray computed tomography apparatus as claimed in claim 1 comprising multiple first transmission/reception devices at said stationary unit, respectively mounted at identical azimuthal angles relative to said axis.

6. An x-ray computed tomography apparatus as claimed in claim 1 comprising multiple second transmission/reception devices at said rotatable unit, respectively mounted at identical azimuthal angles relative to said axis.

7. An x-ray computed tomography apparatus as claimed in claim 1 wherein said at least one first transmission/reception device and said at least one second transmission/reception device are each mounted at the same radial distance from said axis.

8. An x-ray computed tomography apparatus as claimed in claim 1 wherein said at least one first transmission/reception device and said at least one second transmission/reception device are offset from each other in a direction of said axis.

9. An x-ray computed tomography apparatus as claimed in claim 1 comprising at least two first transmission/reception devices at said stationary unit, with transmission between said at least two transmission/reception devices of said stationary unit ensuing through said at least one transmission/reception device of said rotatable unit.

10. An x-ray computed tomography apparatus as claimed in claim 1 wherein each transmission/reception unit emits optical light as said directed signal.

11. An x-ray computed tomography apparatus as claimed in claim 10 wherein each of said transmission/reception units emits a laser beam of optical light as said directed signal.

12. An x-ray computed tomography apparatus as claimed in claim 1 wherein each transmission/reception unit emits said directed signal as a signal comprised of electromagnetic waves, selected from the group consisting of radio waves and Hertzian waves.

13. An x-ray computed tomography apparatus as claimed in claim 1 wherein each transmission/reception unit is a bidirectionally transmitting transmission/reception unit.

14. An x-ray computed tomography apparatus as claimed in claim 1 wherein each transmission/reception unit emits said directed signal as a signal comprised of data packets respectively of a fixed size.

15. An x-ray computed tomography apparatus as claimed in claim 14 wherein each transmission/reception unit adds an appended line to each data packet, selected from the group consisting of a header line and a footer line.

16. An x-ray computed tomography apparatus as claimed in claim 15 wherein each transmission/reception unit comprises an encryption unit that encrypts said data packets.

17. An x-ray computed tomography apparatus as claimed in claim 16 wherein said encryption unit encrypts said data packets according to 8B10B encryption.

18. An x-ray computed tomography apparatus as claimed in claim 1 wherein each transmission/reception unit transmits data at a rate in a range between 1 and 100 Gbps.

19. An x-ray computed tomography apparatus as claimed in claim 1 wherein said detection unit comprises quad-photodetectors.

* * * * *